(12) United States Patent
Frank et al.

(10) Patent No.: US 11,726,077 B2
(45) Date of Patent: Aug. 15, 2023

(54) METHOD FOR CALIBRATING BIOMASS SENSORS OPERATING WITH IMPEDANCE SPECTROSCOPY AND USE OF A SUSPENSION FOR CARRYING OUT SUCH A METHOD

(71) Applicant: Hamilton Bonaduz AG, Bonaduz (CH)

(72) Inventors: Marlene Frank, Bonaduz (CH); Philipp Arquint, Bonaduz (CH); Theo Gaupp, Untervaz (CH)

(73) Assignee: HAMILTON BONADUZ AG, Bonaduz (CH)

( * ) Notice: Subject to any disclaimer, the term of this patent is extended or adjusted under 35 U.S.C. 154(b) by 1312 days.

(21) Appl. No.: 16/081,577

(22) PCT Filed: Mar. 1, 2017

(86) PCT No.: PCT/EP2017/054751
§ 371 (c)(1),
(2) Date: Aug. 31, 2018

(87) PCT Pub. No.: WO2017/149005
PCT Pub. Date: Sep. 8, 2017

(65) Prior Publication Data
US 2019/0079069 A1    Mar. 14, 2019

(30) Foreign Application Priority Data

Mar. 4, 2016 (DE) .................... 10 2016 203 576.2

(51) Int. Cl.
*G01N 33/487* (2006.01)
*G01N 27/02* (2006.01)
*C12M 1/34* (2006.01)

(52) U.S. Cl.
CPC ....... *G01N 33/48735* (2013.01); *C12M 41/36* (2013.01); *G01N 27/026* (2013.01); *C12M 41/46* (2013.01)

(58) Field of Classification Search
CPC .......... G01N 33/48735; G01N 27/026; C12M 41/36; C12M 41/46
See application file for complete search history.

(56) References Cited

U.S. PATENT DOCUMENTS 3,506,544 A * 4/1970 Silverman .............. C12M 41/36
435/14
4,810,963 A    3/1989 Blake-Coleman et al.
(Continued)

FOREIGN PATENT DOCUMENTS

DE    102009007060 A1    12/2010
EP        1 085 316         3/2001
(Continued)

OTHER PUBLICATIONS

O'Brien RW. The Dielectric Response of a Dilute Suspension of Semiconducting Particles. J Colloid Interface Sci. Jan. 15, 1996;177(1):280-281. doi: 10.1006/jcis.1996.0032. PMID: 10479443. (Year: 1996).*
(Continued)

*Primary Examiner* — Yoshihisa Ishizuka
*Assistant Examiner* — Christopher J Gassen
(74) *Attorney, Agent, or Firm* — Tollefson IP

(57) ABSTRACT

A method is provided for calibrating impedance-spectroscopic biomass sensors that are embodied to detect information regarding the quantity and/or size of living cells in a biomass by means of an electric field having a periodically changing field direction
A calibration suspension encompasses an electrically conductive viscously flowable or viscoelastic carrier substance (Continued)

Figure 1:
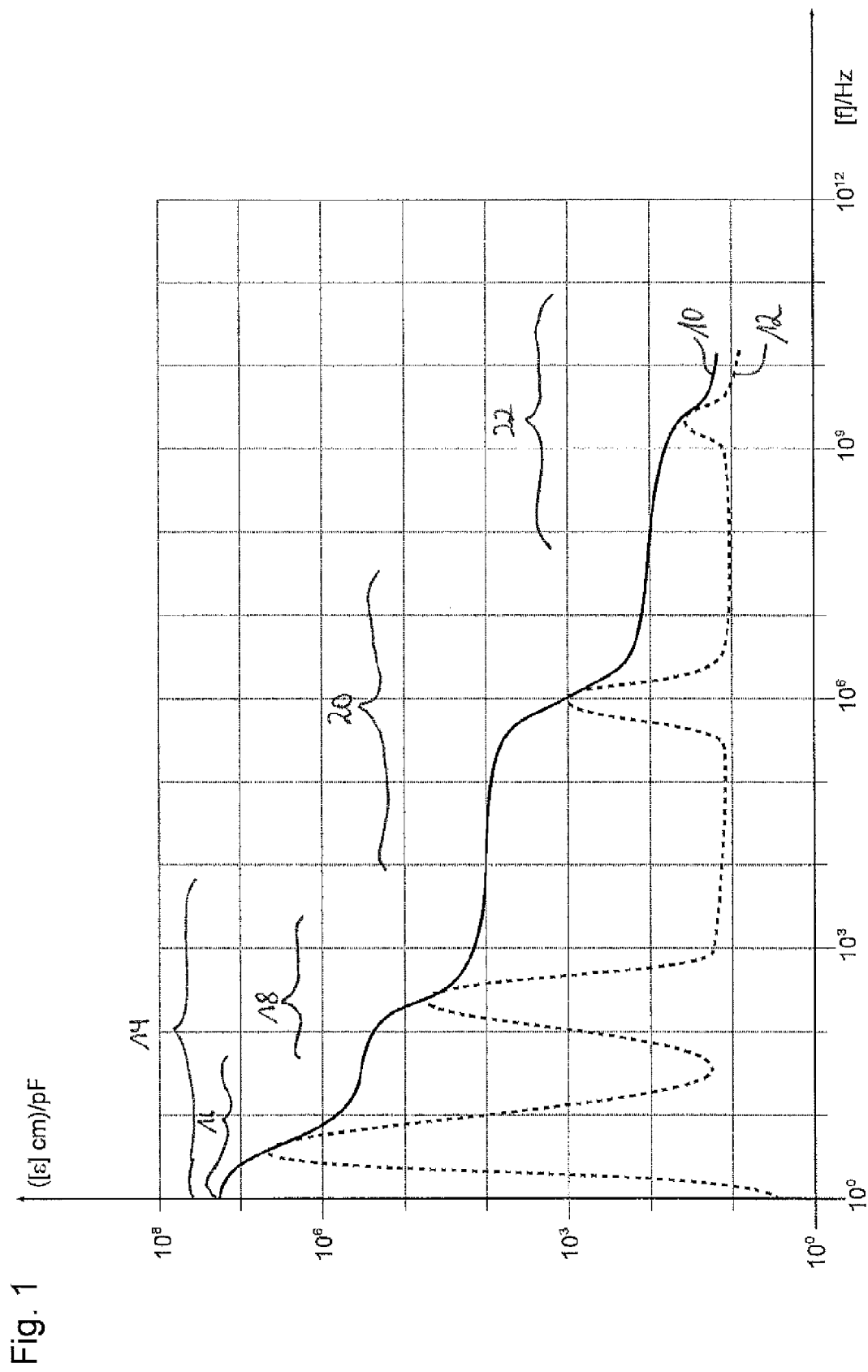

and electrically conductive solid particles and/or solid semiconductor particles received therein.

An electric field is generated having a periodically changing field direction, which acts on the calibration suspension.

At least one permittivity value is detected, respectively representing a permittivity of the calibration suspension, in a context of at least two electric fields having different field direction change frequencies.

A difference value is ascertained that represents a difference between the detected permittivity values.

The difference value is compared with a reference value associated with the calibration suspension.

12 Claims, 2 Drawing Sheets

(56) References Cited

U.S. PATENT DOCUMENTS

| | | | |
|---|---|---|---|
| 4,876,504 A | 10/1989 | Blake | |
| 2008/0262748 A1* | 10/2008 | Ossart | G01N 27/221 324/684 |
| 2008/0312843 A1 | 12/2008 | Esteban et al. | |
| 2011/0316563 A1* | 12/2011 | Davies | G01N 27/226 324/663 |
| 2012/0142032 A1* | 6/2012 | Morgan | G01N 33/585 435/287.2 |
| 2015/0019140 A1* | 1/2015 | Downey | G01N 27/221 702/21 |

FOREIGN PATENT DOCUMENTS

| | | |
|---|---|---|
| EP | 1138758 A1 | 10/2001 |
| WO | 2005/085818 | 9/2005 |

OTHER PUBLICATIONS

C. Brosseau and P. Talbot, "Effective permittivity of nanocomposite powder compacts," in IEEE Transactions on Dielectrics and Electrical Insulation, vol. 11, No. 5, pp. 819-832, Oct. 2004, doi: 10.1109/TDEI.2004.1349787. (Year: 2004).*

R.W. O'Brien, "The Dielectric Response of a Dilute Suspension of Semiconducting Particles", Journal of Colloid and Interface Science, vol. 177, No. 1, 1996, pp. 280-281, doi: 10.1006/jcis.1996. 0032 (Year: 1996).*

Japanese Office Action dated Mar. 22, 2021 for corresponding Japanese patent application.

Dabros M. et al.: "Cole-Cole, linear and multivariate modeling of capacitance data . . . " Bioprocess and Biosystems Engineering, Springer, DE, vol. 32, No. 2, Feb. 1, 2009, 161-173.

Downey, et al., "A novel approach for using dielectric spectroscopy to predict viable cell volume (VCV) in early process development," Biotechnol. Prog., 2014, vol. 30, No. 2 pp. 479-487.

Zhu, et al., "Real-time monitoring of immobilized single yeast cells through multifrequency electrical impedance spectroscopy", Anal Bioanal Chem (2014) 406:7015-7025, pp. 7015-7024.

O'brien, et al., "The Dielectric Response of a Dilute Suspension of Semiconducting Particles", Journal of Colloid and Interface Science 177, 280-281 (1996).

* cited by examiner

METHOD FOR CALIBRATING BIOMASS SENSORS OPERATING WITH IMPEDANCE SPECTROSCOPY AND USE OF A SUSPENSION FOR CARRYING OUT SUCH A METHOD

CROSS REFERENCE TO RELATED APPLICATIONS

This application is the National Stage of International Application No. PCT/EP2017/054751, filed on Mar. 1, 2017, which claims the benefit of German Application No. 10 2016 203 576.2, filed on Mar. 4, 2016. The contents of both applications are hereby incorporated by reference in their entirety.

The present invention relates to a method for calibrating impedance-spectroscopic biomass sensors, and further relates to the use of a suspension for such a calibration method.

Electrical impedance-spectroscopic methods are used as measurement methods for nondestructive in-situ and in-vivo determination of frequency-dependent passive electrical properties of biological materials. One such biological material can be, for example, a substance, referred to hereinafter as "biomass," made up of a liquid and biological cells received therein, for example as obtained from cell culture containers.

The aforementioned frequency-dependent passive electrical properties of the biomass can provide information, inter alia, regarding living-cell count and cell vitality. Further properties of the biomass can also be ascertained by way of the frequency-dependent passive electrical properties, but determination of the number of living cells and of cell vitality has the greatest importance in biotechnology applications.

In very basic and roughly outlined fashion, information regarding the quantity and/or size of living cells in the biomass is detected by impedance spectroscopy as follows: an electric field, whose field direction changes periodically at a predefined frequency, is applied to a suspension of biological cells received in a carrier liquid. Different polarization mechanisms act on the biomass depending on the selected change frequency. The passive electrical properties of biomass, in contrast to exclusively ionic solutions, are therefore frequency-dependent and constitute typical so-called "dispersions." Additional effects occur if living cells are present in the biomass. The living cells represent a barrier to the migration of freely movable ions, so that depending on their cross-sectional area, the cells increase the resistance of the biomass and consequently lower its conductivity. The ions present in the interior of a cell of the biomass are also detected by the electric field. A charge separation occurs at the poorly electrically conducting cell membrane, resulting in polarization at the membrane. The polarization occurs as an electrical double layer. In this situation the current caused by the electric field flows almost exclusively through the extracellular carrier substance of the biomass. The polarization is therefore reflected in an increase in the measurable capacitance, and consequently permittivity, between the field-generating electrodes.

A so-called "alpha dispersion" occurs in the millihertz to kilohertz frequency range, and is caused by the movement and deposition of charge carriers on the cell surface. Active cell membrane effects and active ionic membrane channels also influence the alpha dispersion.

A so-called "beta dispersion," which is based on the capacitive properties of the cell membranes, the intracellular organelles, and the membrane structures themselves, occurs in a frequency range from a few kilohertz to a few hundred megahertz. Fats and proteins in the cell membranes constitute a high-impedance structure. The membrane structures result in so-called "interface" polarization.

The so-called "gamma dispersion," which is brought about by dipolar mechanisms of polar media, for example water and proteins, occurs at even higher frequencies in the range from approx. 0.1 to 100 GHz. At high frequencies, large molecules (such as proteins) having a dipole moment line up in the electric field.

It is principally the beta dispersion range that is of interest for what is particularly relevant for the method of the present Application, namely detecting information regarding the quantity and/or size of living cells in a biomass. For additional information regarding the dispersion ranges of biomasses and the curves of a frequency-dependent permittivity or capacitance which are used to represent them, reference is made to H. P. Schwan, "The practical success of impedance techniques from an historical perspective," in: Proceedings of the X. International Conference on Electrical Bio-Impedance, Barcelona (1998), pp. 3-16; and to H. P. Schwan, "Electrical properties of tissue and cell suspensions," in: Advances in Biological and Medical Physics, Vol. 5 (1957), pp. 147-205.

A known method for impedance-spectroscopic detection of information regarding the quantity and/or size of living cells in a biomass by means of an electric field having a periodically changing field direction is known from U.S. Pat. No. 7,930,110 B2. A biomass sensor usable for such a measurement is known from U.S. Pat. No. 6,596,507 B2. A sensor marketed by the Applicant under the commercial name "Incyte" is also suitable in principle for the measurement method described above.

The situation faced by users of the impedance-spectroscopic measurement technique described above—and "measurement technique" is to be understood very generally with regard to both the method aspect and the sensors used—is that as a rule they must trust the functionality of the sensor, since they usually have no opportunity to check the sensor, in terms of its functionality, in a calibration mode that is informative for subsequent measurement operation.

The object of the present invention is therefore to describe a technical teaching that permits informative calibration of impedance-spectroscopic biomass sensors for detecting information regarding the quantity and/or size of living cells in a biomass by means of an electric field having a periodically changing field direction.

This object is achieved according to the present invention by a method for calibrating impedance-spectroscopic biomass sensors that are embodied to detect information regarding the quantity and/or size of living cells in a biomass by means of an electric field having a periodically changing field direction, encompassing the following steps:

furnishing a calibration suspension encompassing an electrically conductive viscously flowable or viscoelastic carrier substance and electrically conductive solid particles and/or solid semiconductor particles received therein;

generating an electric field, having a periodically changing field direction, which acts on the calibration suspension;

detecting at least one permittivity value, respectively representing a permittivity of the calibration suspension, in a context of at least two electric fields having different field direction change frequencies;

ascertaining a difference value representing a difference between the detected permittivity values;

comparing the difference value with a reference value associated with the calibration suspension.

It has been found that the calibration suspension referred to above, which encompasses an electrically conductive viscously flowable or viscoelastic carrier substance and electrically conductive solid particles and/or solid semiconductor particles received therein, in interaction with biomass sensors embodied for the impedance-spectroscopic instrumental method recited initially for detecting information regarding the quantity and/or size of living cells, yields a response to the periodically changing electric field which is similar to that of the biomass itself. It is thereby possible to infer, from the response of the calibration suspension to the electric field that changes periodically in terms of field direction, the functionality of the biomass sensor being used.

An electric field acting on the calibration suspension and having a periodically changing field direction, which field is similar or identical to the electric field acting on the biomass in the context of real information detection, is therefore generated in the context of the calibration method according to the present invention.

As set forth previously in the context of the presentation of technical correlations of impedance-spectroscopic detection methods, the passive electric properties of the biomass, and thus also of the calibration suspension, which are of interest here are frequency-dependent, so that in order to calibrate the at least one biomass sensor in a context of at least two electric fields having different field direction change frequencies, a respective permittivity value representing a permittivity of the calibration suspension can be detected.

Be it noted here that this does not necessarily mean that the permittivity must be detected directly. As mentioned, it is sufficient to detect a value that represents the permittivity of the calibration suspension. This can be, for example, a capacitance, which as a rule is proportional to the permittivity.

Once the permittivity value has been detected at least two different field direction change frequencies, a difference value that represents a difference between the detected permittivity values can be ascertained. This can be done by simple subtraction of the permittivity values detected at the respective field direction change frequencies.

Because the calibration suspension can be manufactured with predefined chemical and physical properties, it can be designed a priori, for example by way of reference measurements in the laboratory, for a plurality of reference permittivity values or reference value difference values. A reference value of this kind can then be utilized for comparison with the detected difference value. Based on the comparison result then ascertained, the user of the at least one biomass sensor is then able to assess the functionality of the biomass sensor calibrated in accordance with the method recited above.

Assessment of the comparison of the difference value with the reference value associated with the calibration suspension can also be encompassed as an advantageous refinement of the calibration method. This can be done, for example, in fully automated fashion in an evaluation device that is connected in signal-transferring fashion to the at least one biomass sensor. The evaluation device can possess a data memory in which at least the reference value, or a plurality of reference values, associated with the calibration suspension can be stored. For example, a characteristics diagram in which a correlation between permittivity values and field direction change frequencies is described can be stored in the data memory. Instead of a characteristics diagram it is also possible to store a functional correction that enables the evaluation device to calculate a reference value as a function of the field direction change frequencies used in the calibration method.

Comparison of the difference value with the reference difference value is equivalent to a comparison of the detected permittivity values with corresponding reference permittivity values. The latter reference values are then associated with the calibration suspension for those field change frequencies at which the permittivity values are detected during calibration.

The method can furthermore encompass outputting the assessment result to an output device, for example a display screen or a printer.

The advantage of the calibration method according to the present invention is principally that the calibration method can proceed in the same way that the impedance-spectroscopic biomass method also proceeds, using a calibration suspension that does not itself need to contain any biomass, i.e. living or dead cells or cell constituents, and that therefore does not represent a contamination risk for actual biomass. The at least one biomass sensor can consequently contact the calibration suspension at least with a portion, in particular with an instrumentally effective portion, before and/or preferably during generation of the field that changes periodically in terms of its field direction. Because the calibration method therefore corresponds to the real impedance-spectroscopic biomass measurement method except for the suspension constituting the measured specimen, extremely accurate calibration results can be achieved. In addition, it is not necessary to program a separate calibration method sequence for an at least partly automated measurement setup, but instead the sequence of the real measurement method can also be used for calibration.

Results are still obtained if the calibration method is carried out without wetting the biomass sensor with the calibration suspension, but they deviate considerably even though the experimental conditions are substantially identical, and their informative value is therefore reduced as compared with sensor-wetting calibration.

In order to achieve maximally precise calibration results, in a preferred refinement of the invention provision is therefore made that contact between the calibration suspension and at least a portion of the biomass sensor encompasses wetting at least one sensor electrode, preferably all sensor electrodes, of the biomass sensor with calibration suspension. If the biomass sensor comprises more than just one sensor electrode, preferably all sensor electrodes of the biomass sensor which would be wetted with biomass in the context of impedance-spectroscopic detection of the biomass are wetted with calibration suspension.

In order to furnish calibration results that are repeatable and therefore reliable and verifiable, it is preferred if the calibration method encompasses a step of homogenizing the calibration suspension. Depending on the viscosity of the carrier substance, as time passes the solid particles received in the carrier substance can settle and thereby modify the calibration suspension in terms of its response behavior with regard to the external electric field. The homogenizing step can be performed in order to counteract such a sedimentation trend. This homogenization can be accomplished by stirring and/or shaking the calibration suspension. In order to permit detection using a maximally homogeneous calibration suspension, homogenization can occur before, preferably immediately before, the permittivity values are detected.

The duration of the calibration for determining the permittivity values is in a range from 1 to 600 seconds, preferably 1 to 300 seconds, and particularly preferably in a range from 1 to 60 seconds. As little sedimentation as possible should take place over that time span.

Because of its informative value, the aforementioned beta dispersion range is principally of interest for calibration of the impedance-spectroscopic biomass sensors. It is therefore preferred in terms of the calibration method according to the present invention that the permittivity values be detected at frequencies no lower than 50 kHz, preferably no lower than 110 kHz, and particularly preferably no lower than 250 kHz, and no higher than 110 MHz, preferably no higher than 50 MHz, particularly preferably no higher than 30 MHz, in each case including the aforementioned limit values. As a result, the calibration method is performed at frequencies that correspond to those of beta dispersion ranges of an actual biomass that is to be detected.

Not only can a user obtain, with the calibration method, an impression as to the functionality of the at least one impedance-spectroscopic biomass sensor that he or she is using, but he or she can also use the calibration result quantitatively in order to correct any detection errors of the at least one biomass sensor. This too can be accomplished in automated fashion in a control device of the measurement arrangement comprising the at least one biomass sensor, or in the aforementioned evaluation device correlating in signal-transferring fashion with the at least one biomass sensor. According to an advantageous refinement the calibration method can therefore encompass adjusting the biomass sensor, or a data processing apparatus coupled to it in signal-transferring fashion, in accordance with the result of the comparison of the difference value with the reference value. A biomass sensor that would in fact supply an incorrect permittivity value detection result, for example due to a drift error and the like, can thus be adjusted, on the basis of the comparison of the difference value with the reference value, in such a way that the permittivity values detected by it correspond to the permittivity values actually to be expected in the respective measurement circumstances. It is principally—but not only—the ability to adjust the biomass sensor as a function of the comparison result between the difference value and the reference value which creates the capability of ensuring that a correct detection result is always obtained in an impedance-spectroscopic detection method as described previously, provided the biomass sensor is adjustable or exhibits an adjustable error. The calibration method as described and refined above can be carried out for that purpose prior to a real measurement method or a series of real measurement methods carried out on biomass, in order to ensure that the detection results of the at least one measurement method executed after the calibration method are correct.

The present invention therefore also relates to a method for impedance-spectroscopic detection of information regarding the quantity and/or size of living cells in a biomass, encompassing:
  the calibration method as described and refined above;
  subsequently thereto: cleaning of the biomass sensor;
  subsequently thereto: impedance-spectroscopic detection of information regarding the quantity and/or size of living cells in the biomass, by means of the biomass sensor and an electric field, generated thereby, having a periodically changing field direction.

For high-sensitivity impedance-spectroscopic detection applications, provision can even be made not only to carry out a calibration method before impedance-spectroscopic detection using the biomass as measured specimen, but also to carry out a calibration method, as described and refined above, after said detection. It is thereby possible to ensure and verify, for example for documentation and certification purposes, that the biomass sensor has functioned correctly before and after its real detection application to the biomass, and that it can also be expected, with a probability approaching certainty, that it has functioned correctly during impedance-spectroscopic detection.

The essence of the calibration method is replacing the biomass, as measured specimen, with the calibration suspension, which can be manufactured with a defined composition devoid of biological constituents and thus precludes cross-contamination of biomass with other biomass. The present invention therefore also relates to the use of a suspension, encompassing an electrically conductive viscously flowable or viscoelastic carrier substance and electrically conductive solid particles and/or solid semiconductor particles received therein, to calibrate impedance-spectroscopic biomass sensors that are embodied to detect information regarding the quantity and/or size of living cells in a biomass by means of an electric field having a periodically changing field direction.

In order to ensure that the solid particles in the calibration suspension exhibit a merely negligible sedimentation tendency at least for the duration of the calibration method, the calibration suspension preferably comprises a carrier substance having a dynamic viscosity of no less than 1 Pas, preferably no less than 50 Pas, and of no more than 50,000 Pas, preferably no more than 10,000 Pas, particularly preferably no more than 1000 Pas, measured with a rotational viscometer.

For controlled setting of a dynamic viscosity of the carrier substance, the latter can encompass a base liquid and a thickening agent. The base liquid can be water.

The thickening agent can be selected from a group encompassing a biopolymer, for example a polysaccharide, in particular glycogen, starch, pectin, xanthan, carrageenan, guar gum, gum arabic, cellulose or a cellulose derivative, for example carboxymethyl cellulose, lignin, chitin, chitosan, gelatin, agar-agar, an alginate, or a polymer, for example polyvinylpyrrolidone, polyDADMAC or polyAMPS, or glycol.

Instead of a base liquid thickened by a thickening agent, the carrier substance can also encompass or be a polymer and/or a gel. A so-called hydrogel can be used in particular as a gel.

Be it also noted that all indications given in the present Application regarding physical parameters of the calibration suspension, of the solid particles received therein, and of the carrier substance, were ascertained or are to be ascertained for comparison at room temperature and in a standard atmosphere of 1013 hPa.

As has been stated previously, it is important in terms of the usability of the carrier substance that it be electrically conductive. Carrier substances whose electrical conductivity is in the range from 0.01 to 500 mS/cm, preferably in the range from 0.1 to 200 mS/cm, particularly preferably in the range from 1 to 50 mS/cm, have proven to be particularly suitable. Highly preferably, the conductivity can even be in a range from 1 to 10 mS/cm.

For all the range indications in this application, the limits indicated are always understood to be encompassed by the range.

This electrical conductivity can be established by the fact that the carrier substance comprises movable ions of opposite charge polarity, for example due to the dissolution or melting of salts and/or protolysis of acids or bases. Dissolution of salts is preferred to melting thereof due to the thermal boundary conditions necessary for that purpose.

In order to rule out the possibility that the change in the ion content of the carrier substance, and thus of the calibration suspension, might influence the calibration result, according to an advantageous refinement of the use of the calibration suspension, provision is made that the concentration of ions of opposite charge polarity in the carrier substance is saturated in permittivity-related fashion in such a way that under otherwise identical conditions, an elevation of the ion concentration in the carrier substance does not cause any elevation of the permittivity value of the calibration suspension. The conditions are, in particular, conditions for detecting the permittivity of the calibration suspension.

The particle size range that is usable for solid particles received or to be received in the carrier substance extends from 0.01 μm to 500 μm. Preferably, solid particles having a particle size in the range from 0.1 μm to 200 μm are used in the calibration suspension. This can also depend on the respective material of the solid particles. Particularly preferably, fine solid particles having a particle size in the range from 1 μm to 20 μm are received in the carrier substance in order to constitute the calibration suspension. The particle size can be determined by sieving. If the particle size cannot be determined with sufficient accuracy by sieving, it can be done by dynamic light scattering.

For example, aluminum powder (aluminum particles) can be used as solid particles having a particle size of 100 to 200 μm. Graphite powder (graphite particles) is preferably received in the carrier substance as solid particles, a preferred particle size in the range from 1 to 20 μm being used for graphite particles. Activated carbon particles can also be received as solid particles in the carrier substance in order to constitute a calibration suspension. With activated carbon particles, the preferred particle size range extends from 2 to 12 μm.

The solid particles can be constituted from a material having an electrical conductivity in the range from $5 \times 10^{-3}$ S/m to $7 \times 10^7$ S/m, preferably in the range from $1 \times 10^4$ S/m to $4 \times 10^6$ S/m.

Tellurium can be used, for example, as a semiconductor constituting a solid particle material. Its electrical conductivity of approximately $5 \times 10^{-3}$ S/m is at the lower end of the aforesaid range. Silver, for example, is at the upper end of the aforesaid conductivity range, at somewhat less than $7 \times 10^7$ S/m. Further possible and indeed preferred materials for the solid particles of the calibration suspension are silicon carbide having a conductivity of 50 S/m, aluminum at somewhat less than $4 \times 10^6$ S/m, activated carbon at approximately $2 \times 10^4$ S/m, platinum at somewhat more than $9 \times 10^6$ S/m. Graphite is used particularly preferably as a solid particle material. Graphite has an electrical conductivity, in its conductivity direction parallel to its flat layers, of $3 \times 10^6$ S/m.

With regard to its nature, a suitable solid particle material can encompass a metal and/or a semi-metal and/or a semiconductor material and/or a conductive organic material and/or graphite and/or activated carbon, or can be made of at least one such material. The calibration suspension is preferably devoid of cell material such as cells, cell membranes, and the like.

In order to complete the technical teaching, the present invention also relates to a calibration arrangement encompassing:
- a calibration suspension as described and refined above;
- an impedance-spectroscopic biomass sensor that is embodied to detect information regarding the quantity and/or size of living cells in a biomass by means of an electric field having a periodically changing field direction; and
- a data processing device that is embodied to process sensor signals delivered operationally by the biomass sensor, and that is embodied in particular to carry out the method described and refined above.

Figure 2:
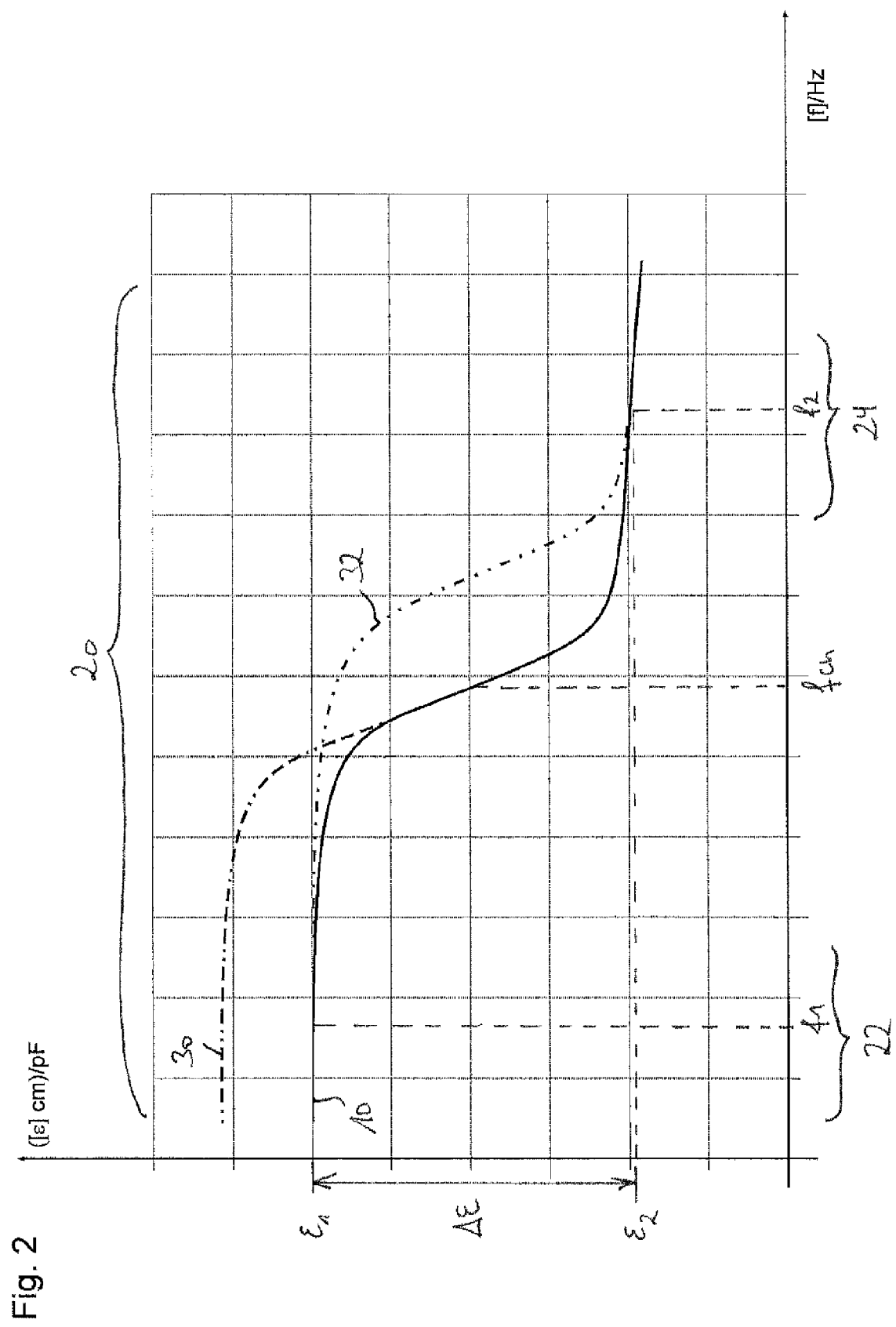

The present invention will be explained in further detail below with reference to the appended drawings, in which:

FIG. 1 schematically depicts a correlation of the frequency dependence of the permittivity of a biomass; and FIG. 2 schematically depicts the frequency-dependent permittivity of the biomass in the beta-dispersion range that is of particular interest.

FIG. 1 depicts, very generally and merely schematically, the frequency dependence of the permittivity of a biomass, i.e. for example of a liquid containing biological cells. Solid line 10 shows the real part of the permittivity ε as a function of frequency f; dashed line 12 shows the imaginary part of the frequency-dependent permittivity ε.

The graphs are obtained by applying to a biomass an electric field whose field direction is periodically changed or reversed. The frequency f of the field direction change is plotted, in units of Hz, along the abscissa of the diagram of FIG. 1. The permittivity ε, in units of pF/cm, is plotted in the ordinate direction.

When the frequency f is gradually elevated over a wide frequency range, different polarization effects occur in the biomass as a result of the constituents contained therein, and result in a change in the permittivity (and also capacitance) between the field-generating electrodes. The individual recognizable steps in the permittivity/frequency curve of a biomass are referred to, after H. P. Schwan, as alpha, beta, and gamma dispersions. The alpha dispersion (see alpha dispersion range 14 in FIG. 1) occurs at frequencies in the millihertz to kilohertz range. As currently understood, the alpha dispersion is produced by the movement and deposition of charge carriers on the surface of cells. The alpha dispersion is also influenced by active cell membrane effects and active ionic membrane channels.

In FIG. 1, frequency range 14 of the alpha dispersion comprises two sub-dispersions alpha1 indicated by range 16, and alpha2 indicated by range 18.

Frequency range 20 of the beta dispersion is in the range from a few kilohertz to approximately 100 MHz, and derives from the capacitive properties of cell membranes, for example because fats and proteins form a high-impedance structure, and further derives from the intracellular organelles and membrane structures where interfacial polarization occurs in the aforesaid frequency range.

The gamma dispersion occurs in frequency range 22 from approximately 0.1 to 100 GHz. It is brought about by dipolar mechanisms of polar media such as water and the proteins that are also contained in biomass. This is an orientation polarization, produced by large molecules that have a dipole moment and align themselves at high frequencies.

The real part 10 of permittivity ε exhibits, at the characteristic frequencies of the respective dispersions, an inflection point that is usually located between two plateau-like frequency ranges. The imaginary part of the permittivity ε exhibits a local maximum at the respective characteristic frequency of a dispersion.

Whereas the gamma dispersion in frequency range 22 can be utilized for determination of the water content of biological specimens because of the polarization effects that occur in it, the beta dispersion range in frequency range 20 is of great interest for the assessment of biomass, since the permittivity ε, in particular its real part, in beta dispersion range 20 provides information regarding cell activity, cell size, and the number of living cells contained in the biomass.

In FIG. 2, the real part of a frequency-dependent permittivity ε of a biomass is plotted in entirely qualitative fashion.

The following information can be obtained qualitatively from curve 10 for the real part of the permittivity as a function of frequency f: FIG. 2 shows qualitatively that a frequency $f_{Ch}$ that is characteristic for beta dispersion range 20 is preceded by a plateau region 22 in which permittivity c changes very little with frequency as compared with the region around the characteristic frequency $f_{Ch}$, and that the characteristic frequency $f_{Ch}$ is followed by a further plateau region 24 which is different from plateau region 22 preceding characteristic frequency $f_{Ch}$ and in which the permittivity ε, once again as compared with the region around characteristic frequency $f_{Ch}$, likewise does not change greatly with frequency.

If a permittivity value $\varepsilon_1$ representing the permittivity ε (more precisely its real part) is therefore detected at a frequency $f_1$ in plateau region 22, as well as a permittivity value $\varepsilon_2$ at a frequency $f_2$ in plateau region 24, it is then possible to ascertain, from the permittivity values $\varepsilon_1$ and $\varepsilon_2$ ascertained respectively at the two frequencies $f_1$ and $f_2$, a difference value $\Delta\varepsilon$ between the two permittivity values, difference value $\Delta\varepsilon$ being an indication of the number of living cells contained in the biomass. The alternative permittivity curve 30, indicated with two dots and three dashes, would result in a $\Delta\varepsilon$ having a greater magnitude at the respective measurement frequencies $f_1$ and $f_2$, which allows the conclusion that the biomass for which permittivity curve 30 was obtained comprises more living cells in the same volume than the biomass on which permittivity curve 10 is based.

In the interest of completeness, be it noted that a change in the characteristic frequency $f_{Ch}$ indicates a change in the size of the cells or in their physiology. A permittivity curve 32 having two dots and a dash has a higher characteristic frequency in FIG. 2.

The slope of the permittivity curve at the location of its characteristic frequency $f_{Ch}$ is an indication of the cell size distribution: an increasing slope indicates a more highly heterogeneous cell size distribution, and profiles of permittivity curve 10 which become flatter at the location of characteristic frequency $f_{Ch}$ signify more-homogeneous cell size distributions.

If the beta dispersion region is known to some degree for a biomass that is to be detected instrumentally, frequencies $f_1$ and $f_2$ are known as measurement points.

The calibration suspension described in this Application supplies, at the respective measurement frequencies $f_1$ and $f_2$, defined different permittivity values $\varepsilon_1$ and $\varepsilon_2$ that result in a likewise defined difference value $\Delta\varepsilon$.

Because the calibration suspension is known in terms of the materials used (carrier substance and solid particles) and in terms of the quantitative ratios used in producing the suspension, it can be reproduced with high accuracy.

Reference values that can comprise a value pair, for example measurement frequency and permittivity value measured at that frequency, can thus be associated with the calibration suspension by way of corresponding measurements of permittivity values at different frequencies. The reference values can be statistically confirmed by repeating the measurements several times. The variability of the reference values around a reference value mean can therefore also be known.

It is thus possible to ascertain from the associated reference values, for a predetermined calibration suspension at predetermined different measurement frequencies $f_1$ and $f_2$, the reference difference value of the permittivity values which is to be utilized for calibration. Carrying out a calibration measurement method using the biomass sensors that are to be calibrated, but using the defined calibration suspension instead of the biomass, thus allows a difference value of the permittivity values to be detected sensorially and compared with the reference difference value. Based on the degree of agreement between the reference difference value and the difference value detected in the calibration method, it is then possible to infer the functionality of the biomass sensors used in the calibration method; or the biomass sensors can be correspondingly adjusted so that the difference value of the calibration permittivity values which it supplies under defined calibration conditions agrees with the corresponding reference difference value.

The calibration method, optionally followed by the adjustment method, can be carried out at regular intervals or can be carried out every time before sensorial detection of a biomass is carried out.

The calibration method can also be carried out after sensorial detection of a biomass in order to verify that the functionality of the biomass sensors has not changed during the measurement method.

A variety of calibration suspensions, which differ in terms of carrier substance and/or solid particles and/or in terms of the quantity of solid particles received in the carrier substance, can be furnished for the calibration of biomass sensors. It is thereby possible to perform a calibration using an appropriately selected calibration suspension that is as similar as possible to the measurement method carried out for sensorial detection of the biomass. The informative value of the calibration method for a measurement method carried out using the same biomass sensors can thereby advantageously be increased.

The invention claimed is:

1. A method for calibrating an impedance-spectroscopic biomass sensor that is embodied to detect information regarding the quantity and/or size of living cells in a biomass by means of an electric field having a periodically changing field direction, comprising the following steps:

furnishing a calibration suspension, which is devoid of biological constituents in a form of living or dead cells and comprising an electrically conductive viscously flowable or viscoelastic carrier substance having an electrical conductivity in the range of 1 to 50 mS/cm, and electrically conductive solid particles and/or solid semiconductor particles received therein;

generating an electric field, having a periodically changing field direction at a frequency in the range of 50 kHz to 50 MHz, which acts on the calibration suspension;

detecting at least one permittivity value, respectively representing a permittivity of the calibration suspension, for each of at least two electric fields having different field direction change frequencies;

ascertaining a difference value representing a difference between the detected permittivity values; and comparing the difference value with a reference value associated with the calibration suspension.

2. The calibration method according to claim 1, further comprising, before or during generation of the electric field, contact between the calibration suspension and at least a portion of the impedance-spectroscopic biomass sensor.

3. The calibration method according to claim 2, wherein contact between the calibration suspension and at least a portion of the impedance-spectroscopic biomass sensor includes wetting at least one sensor electrode of the impedance-spectroscopic biomass sensor with calibration suspension.

4. The calibration method according to claim 2, wherein contact between the calibration suspension and at least a portion of the biomass sensor encompasses wetting all sensor electrodes of the impedance-spectroscopic biomass sensor with calibration suspension.

5. The calibration method according to claim 1, further comprising a step of homogenizing the calibration suspension, by stirring and/or shaking the calibration suspension.

6. The calibration method according to claim 5, wherein the homogenizing step is performed before detection of the permittivity values.

7. The calibration method according to claim 5, wherein the homogenizing step is performed immediately before detection of the permittivity values.

8. The calibration method according to claim 1, further comprising adjusting the impedance-spectroscopic biomass sensor, or a data processing apparatus coupled to the impedance-spectroscopic biomass sensor in signal-transferring fashion, in accordance with a result of the comparison of the difference value with the reference value.

9. A method for impedance-spectroscopic detection of information regarding the quantity and/or size of living cells in a biomass, comprising the steps of:
  performing the calibration method according to claim 1;
  subsequently thereto: cleaning of the impedance-spectroscopic biomass sensor;
  subsequently thereto: impedance-spectroscopic detection of information regarding the quantity and/or size of living cells in the biomass, by means of the impedance-spectroscopic biomass sensor and an electric field, generated thereby, having a periodically changing field direction.

10. The method for impedance-spectroscopic detection of information regarding the quantity and/or size of living cells in a biomass according to claim 9, further comprising subsequently thereto: performing the calibration method according to claim 1.

11. A calibration arrangement, comprising:
  an impedance-spectroscopic biomass sensor that is embodied to detect information regarding the quantity and/or size of living cells in a biomass by means of an electric field having a periodically changing field direction at a frequency in the range of 50 kHz to 50 MHz;
  a calibration suspension being devoid of biological constituents in a form of living or dead cells and comprising an electrically conductive viscously flowable or viscoelastic carrier substance having an electrical conductivity in a range from 1 to 50 mS/cm and electrically conductive solid particles and/or solid semiconductor particles received therein, to calibrate the impedance-spectroscopic biomass sensor; and
  a data processing device that is embodied to process sensor signals delivered operationally by the impedance-spectroscopic biomass sensor, and that is embodied in particular to carry out the method according to claim 1.

12. The calibration method according to claim 1, wherein the calibration suspension comprises an electrically conductive viscously flowable or viscoelastic carrier substance and electrically conductive solid particles and/or solid semiconductor particles received therein, to calibrate the impedance-spectroscopic biomass sensor that is embodied to detect information regarding the quantity and/or size of living cells in a biomass by means of an electric field having a periodically changing field direction.

* * * * *